United States Patent [19]
Sutton et al.

[11] Patent Number: 6,103,112
[45] Date of Patent: Aug. 15, 2000

[54] MIPC CHROMATOGRAPHIC APPARATUS WITH IMPROVED TEMPERATURE CONTROL

[75] Inventors: John E. Sutton, Bellevue, Nebr.; Douglas T. Gjerde, Saratoga; Paul D. Taylor, Palo Alto, both of Calif.

[73] Assignee: Transgenomic, Inc., San Jose, Calif.

[21] Appl. No.: 09/295,474

[22] Filed: Apr. 19, 1999

Related U.S. Application Data

[63] Continuation-in-part of application No. 09/081,040, May 18, 1998, which is a continuation-in-part of application No. 08/748,376, Nov. 13, 1996, Pat. No. 5,772,889, and application No. 09/129,105, Aug. 4, 1998

[60] Provisional application No. 60/099,825, Sep. 10, 1998, provisional application No. 60/119,936, Feb. 12, 1999, provisional application No. 60/054,788, Aug. 5, 1997, provisional application No. 60/056,012, Aug. 18, 1997, provisional application No. 60/056,500, Aug. 20, 1997, provisional application No. 60/061,445, Oct. 9, 1997, provisional application No. 60/062,690, Oct. 22, 1997, provisional application No. 60/067,269, Dec. 3, 1997, provisional application No. 60/070,572, Jan. 6, 1998, provisional application No. 60/070,585, Jan. 6, 1998, and provisional application No. 60/093,844, Jul. 22, 1998.

[51] Int. Cl.$^7$ ................................................ B01D 15/08
[52] U.S. Cl. ..................... 210/198.2; 210/656; 210/175; 95/87; 96/101
[58] Field of Search .................................. 210/656, 175, 210/180, 181, 198.2; 95/87; 96/101, 102, 103

[56] References Cited

U.S. PATENT DOCUMENTS

| | | | |
|---|---|---|---|
| 5,585,236 | 12/1996 | Bonn et al. | 435/5 |
| 5,641,400 | 6/1997 | Kaltenbach | 210/198.2 |
| 5,646,048 | 7/1997 | Templin | 210/198.2 |
| 5,744,029 | 4/1998 | Li | 210/198.2 |
| 5,795,976 | 8/1999 | Oefner et al. | 536/25.4 |
| 5,830,353 | 11/1998 | Henderson | 210/198.2 |
| 5,935,522 | 8/1999 | Sweedlow | 210/198.2 |
| 6,030,527 | 2/2000 | Gaerde | 210/198.2 |

OTHER PUBLICATIONS

DHPLC Workshop, Standford University, CA, pp. 32–43 (Mar. 17, 1997).

Djordjevic et al, HPLC Separation of Oligonucleotides in Isocratic and Temperature–Programming Mode, Analytical Chemistry, 70: 1921–1925 (1998).

Hayward–Lester et al, Rapid Quantification of Gene Expression by competitive PT–PCR and Ion–Pair Reversed–Phase HPLC, BioTechniques, 20: 250–257 (1996).

(List continued on next page.)

*Primary Examiner*—Ernest G. Therkorn
*Attorney, Agent, or Firm*—William B. Walker

[57] ABSTRACT

A liquid chromatography apparatus with stationary and mobile phase temperature controls suitable for polynucleotide separations by MIPC and DMIPC processes. The apparatus includes heater means with a temperature control system; a matched ion polynucleotide chromatography separation column having an inlet end; a coil of capillary tubing having an inlet end and an outlet end. The outlet end of the capillary tubing is connected with the inlet end of the separation column. The inlet end of the capillary tubing comprising means for receiving process liquid, the tubing having a length of from 6 to 400 cm having a linear tubing length of heating means. The separation column and the coil of capillary tubing are enclosed in the heater means. The capillary tubing preferably is PEEK or titanium. The heater means can be an air batch oven. Preferably, it is a heat-conducting block having a first heat transfer surface, a separation column receptacle, and a capillary coil receptacle. A separation column is positioned within the separation column receptacle in heat conducting relationship with an inner wall thereof. A coil of capillary tubing is positioned in the capillary coil receptacle, the outer extremities of the coil being in heat conducting relationship with an inner wall of the capillary coil receptacle. Optimally, the heating means is a Peltier heating and cooling unit in heat conducting relationship with a heat transfer surface of the heating block.

8 Claims, 5 Drawing Sheets

OTHER PUBLICATIONS

Lim, Sharon, DNA Denaturation Using the Cary 1/3 Ther

Huber et al, High–Resolution Liquid Chromatography of Oligonucleotides on Nonporous Alkylated Styrene–Divinylbenzene Copolymers, Analytical Biochemistry, 212: 351–358 (1993).

Huber et al, Rapid Analysis of Biopolymers on Modified Non–Porous Polystyrene–Divinylbenzene Particles, Chromatographia, vol. 37 No. 11/12: 653–658 (Dec. 1993).

Kuklin et al, Detection of Single–Nucleotide Polymorphisms with the Wave(™) DNA Fragment Analysis System, Genetic Testing, vol. 1, No. 3: 201–206 (1997).mal Analysis System, Varian Cor. Technical Note, Jun. 1991, pp. 1–5.

Oefner et al, High–Resolution Liquid Chromatography of Nucleic Acids, American Laboratory, 28C–28J (Jun. 1994).

Wells et al. RPC–5 Column Chromatography for the Isolation of DNA Fragments, Methods of Enzymology, vol. 65, Nucleic Acids, Part I, pp. 327–347, 1980.

Cooper et al, An Estimate of Unique DNA Sequence Heterozygosity in the Human Genome, Human Genetics, vol. 69 pp. 201–205, Jan. 1, 1985.

Cotton et al, Slowly by Surely Towards Better Scanning for Mutations, TIG, vol. 13 No. 2: 43–46 (Feb. 1997).

Guyer et al, How is the Human Genome Project Doing, and What Have We Learned So Far?, Proc. Natl. Acad. Sci., vol. 92, pp 10841 –10848 Nov. 1, 1995.

Hayward–Lester et al, Accurate and Absolute Quantitative Measurement of Gene Expression by Single–Tube RT–PCR and HPLC, Genome Research, No. 5: 494–499 (1995).

Liu et al, Denaturing High Performance Liquid Chromatography (DHPLC) Used in the Detection of Germline and Somatic Mutaions, Nucleic Acid Research, vol. 26 No. 6: 1396–1400 (1998).

Underhill et al, A Pre–Columbian Y Chrromosome–Specific Transition and its implications for Human Evolutionary History, Proc. Natl. Acad. Sci., 93: 196–200 (Jan. 1996).

Underhill et al, Detection of Numerous Y Chromosome Biallelic Polymorphisms by Denaturing High–Performance Liquid Chromatography, Genome Research, No. 7: 996–1005 (1997).

MIPC CHROMATOGRAPHIC APPARATUS WITH IMPROVED TEMPERATURE CONTROL

RELATIONSHIP TO COPENDING APPLICATIONS

This application claims priority from Provisional Application Ser. No. 60/099,825 filed Sep. 10, 1998 and Provisional Application Ser. No. 60/119936 filed Feb. 2, 1999. Furthermore, this application is a continuation-in-part of U.S. patent applications Ser. No. 09/081,040 filed May 18, 1998 which is, in turn, a Continuation-in-Part of U.S. patent application Ser. No. 08/748,376 filed Nov. 13, 1996 (now U.S. Pat. No. 5,772,889); and Ser. No. 09/129,105 filed Aug. 4, 1998 which claims priority from copending, commonly assigned Provisional Applications Ser. Nos. 60/054,788 filed Aug. 5, 1997; Ser. No. 60/056,012 filed Aug. 18, 1997; Ser. No. 60/056,500 filed Aug. 20, 1997; Ser. No. 60/061,445 filed Oct. 9, 1997; Ser. No. 60/062,690 filed Oct. 22, 1997; Ser. No. 60/067,269 filed Dec. 3, 1997; Ser. No. 60/070,572 filed Jan. 6, 1998; Ser. No. 60/070,585 filed Jan. 6, 1998 and Ser. No. 60/093,844 filed Jul. 22, 1998. The entire disclosures of the above-listed patent and applications are hereby incorporated by reference.

This application is related to co-pending, commonly assigned U.S. patent application Ser. No. 09/058,580 filed Mar. 10, 1998, Ser. No. 09/058,337 filed Mar. 10, 1998, Ser. No. 09/065,913 filed Apr. 24, 1998, Ser. No. 09/081,039 filed May 18, 1998, Ser. No. 09/081,040 filed May 18, 1998, and Ser. No. 09/080,547 filed May 18, 1998, the entire disclosures of all of which are incorporated herein by reference.

FIELD OF THE INVENTION

The invention concerns a high pressure chromatographic separation system denoted herein as Matched Ion Polynucleotide Chromatography (MIPC) to distinguish it from traditional partitioning-based, reverse phase HPLC systems. In particular, this invention relates to MIPC chromatographic systems with improved, high precision column heater systems.

BACKGROUND OF THE INVENTION

Traditional chromatography is a separation process based on partitioning of mixture components between a "stationary phase" and a "mobile phase". The stationary phase is provided by the surface of solid materials which can comprise many different materials in the form of particles or passageway surfaces of cellulose, silica gel, coated silica gel, polymer beads, polysaccharides, and the like. These materials can be supported on solid surfaces such as on glass plates or packed in a column. The mobile phase can be a liquid or a gas in gas chromatography. This invention relates to liquid mobile phases.

The separation principles are generally the same regardless of the materials used, the form of the materials, or the apparatus used. The different components of a mixture have different respective degrees of solubility in the stationary phase and in the mobile phase. Therefore, as the mobile phase flows over the stationary phase, there is an equilibrium in which the sample components are partitioned between the stationary phase and the mobile phase. As the mobile phase passes through the column, the equilibrium is constantly shifted in favor of the mobile phase. This occurs because the equilibrium mixture, at any time, sees fresh mobile phase and partitions into the fresh mobile phase. As the mobile phase is carried down the column, the mobile phase sees fresh stationary phase and partitions into the stationary phase. Eventually, at the end of the column, there is no more stationary phase and the sample simply leaves the column in the mobile phase.

A separation of mixture components occurs because the mixture components have slightly different affinities for the stationary phase and/or solubilities in the mobile phase, and therefore have different partition equilibrium values. Therefore, the mixture components pass down the column at different rates.

Since chromatographic separations depend on interactions with the stationary phase, it is known that one way for improving separation is increasing the surface area of the stationary phase. The best separations are obtained when the interactions are low, i.e., the partitioning coefficient is low and the column is long, providing increased interactions.

In traditional liquid chromatography, a glass column is packed with stationary phase particles and mobile phase passes through the column, pulled only by gravity. However, when smaller stationary phase particles are used in the column, the pull of gravity alone is insufficient to cause the mobile phase to flow through the column. Instead, pressure must be applied. However, glass columns can only withstand about 200 psi. Passing a mobile phase through a column packed with 5 micron particles requires a pressure of about 2000 psi or more to be applied to the column. 5 to 10 micron particles are standard today. Particles smaller than 5 microns are used for especially difficult separations or certain special cases). This process is denoted by the term "high pressure liquid chromatography" or HPLC.

HPLC has enabled the use of a far greater variety of types of particles used to separate a greater variety of chemical structures than was possible with large particle gravity columns. The separation principle, however, is still the same.

An HPLC-based ion pairing chromatographic method was recently introduced to effectively separate mixtures of double stranded polynucleotides in general, and DNA in particular, wherein the separations are based on base pair length (U.S. Pat. No. 5,585,236 to Bonn (1996); Huber, et al., *Chromatographia* 37:653 (1993); Huber, et al., *Anal. Biochem.* 212:351 (1993)). These references and the references contained therein are incorporated herein in their entireties. The term "Matched Ion Polynucleotide Chromatography" (MIPC) has been applied to this method by the Applicants as their understanding of the DNA separation mechanism has evolved. MIPC separates DNA fragments on the basis of base pair length and is not limited by the deficiencies associated with gel based separation methods.

Matched Ion Polynucleotide Chromatography, as used herein, is defined as a process for separating single and double stranded polynucleotides using non-polar separation media, wherein the process uses a counter-ion agent, and an organic solvent to release the polynucleotides from the separation media. Basic MIPC separations are complete in less than 10 minutes, and frequently in less than 5 minutes. For more difficult separations such as separations using socratic solvent condition, the separation time will be longer. Effective isocratic and target zone elutions require precise control of the separation conditions.

As the use and understanding of MIPC developed, it was discovered that when MIPC analyses were carried out at a partially denaturing temperature, i.e., a temperature sufficient to denature a heteroduplex at the site of base pair mismatch, homoduplexes could be separated from heteroduplexes having the same base pair length (U.S. Pat. No. 5,795,976; Hayward-Lester, et al., *Genome Research* 5:494 (1995); Underhill, et al., *Proc. Natl. Acad. Sci. USA* 93:193 (1996); Doris, et al., *DHPLC Workshop*, Stanford University, (1997)). These references and the references contained therein are incorporated herein in their entireties. Thus, the use of Denaturing HPLC (DHPLC) was applied to mutation detection (Underhill, et al., *Genome Research* 7:996 (1997); Liu, et al., *Nucleic Acid Res.*, 26;1396 (1998)).

DHPLC can separate heteroduplexes that differ by as little as one base pair. However, separations of homoduplexes and heteroduplexes can be poorly resolved. Artifacts and impurities can also interfere with the interpretation of DHPLC separation chromatograms in the sense that it may be difficult to distinguish between an artifact or impurity and a putative mutation (Underhill, et al., *Genome Res.* 7:996 (1997)). The presence of mutations may even be missed entirely (Liu, et al., *Nucleic Acid Res.* 26:1396 (1998)). The references cited above and the references contained therein are incorporated in their entireties herein.

The accuracy, reproducibility, convenience and speed of DNA fragment separations and mutation detection assays based on DHPLC have been compromised in the past because of DHPLC system related problems. Important aspects of DNA separation and mutation detection by HPLC and DHPLC which have not been heretofore addressed include the treatment of materials comprising chromatography system components; the treatment of materials comprising separation media; solvent pre-selection to minimize methods development time; optimum temperature pre-selection to effect partial denaturation of a heteroduplex during MIPC; and optimization of DHPLC for automated high throughput mutation detection screening assays. These factors are essential in order to achieve unambiguous, accurate, reproducible and high throughput DNA separations and mutation detection results.

A need exists, therefore, for an HPLC system which can separate DNA fragments based on size differences, and can also separate DNA having the same length but differing in base pair sequence (mutations from wild type), in an accurate, reproducible, reliable manner. Such a system should be automated and efficient, should be adaptable to routine high throughput sample screening applications, and should provide high throughput sample screening with a minimum of operator attention.

The basic MIPC separation process differs from the traditional HPLC separation processes in that the separation is not achieved by a series of equilibrium separations between the mobile phase and the stationary phase as the liquids pass through the column. Instead, the sample is fed into the column using a solvent strength which permits the sample dsDNA to bind to the separation media surface. Strands of a specific base pair length are irreversibly removed from the stationary phase surface and are carried down the column by a specific solvent concentration. By passing an increasing gradient of solvent through the sample, successively larger base pair lengths are removed in succession and passed through the column. When DNA is released from the stationary phase, its linear velocity quickly reaches the linear velocity of the mobile phase. The basic separation is not column length or stationary phase area dependent.

An isocratic variation of the MICP process can be applied to separate mixtures of DNA fragments having the same size, where fragments in the mixture exhibit differences in the degree of non-polarity.

The application of the Matched Ion Polynucleotide Chromatography (MIPC) under the partially denaturing conditions used for separating heteroduplexes from homoduplexes in mutation detection is hereafter referred to as DMIPC.

Separation of double-stranded deoxyribonucleic acids (dsDNA) fragments and detection of DNA mutations is of great importance in medicine, in the physical and social sciences, and in forensic investigations. The Human Genome Project is providing an enormous amount of genetic information and yielding new information for evaluating the links between mutations and human disorders (Guyer, et al., *Proc. Natl. Acad. Sci. USA* 92:10841 (1995)). For example, the ultimate source of disease is described by genetic code that differs from the wild type (Cotton, *TIG* 13:43 (1997)). Understanding the genetic basis of disease can be the starting point for a cure. Similarly, determination of differences in genetic code can provide powerful and perhaps definitive insights into the study of evolution and populations (Cooper, et. al., *Human Genetics* vol. 69:201 (1985)). Understanding these and other issues related to genetic coding requires the ability to identify anomalies, i.e., mutations, in a DNA fragment relative to the wild type.

DNA molecules are polymers comprising sub-units called deoxynucleotides. The four deoxynucleotides found in DNA comprise a common cyclic sugar, deoxyribose, which is covalently bonded to any of the four bases, adenine (a purine), guanine (a purine), cytosine (a pyrimidine), and thymine (a pyrimidine), referred to herein as A, G, C, and T respectively. A phosphate group links a 3'-hydroxyl of one deoxynucleotide with the 5'-hydroxyl of another deoxynucleotide to form a polymeric chain. In double stranded DNA, two strands are held together in a helical structure by hydrogen bonds between what are called complimentary bases. The complimentarity of bases is determined by their chemical structures. In double stranded DNA, each A pairs with a T and each G pairs with a C, i.e., a purine pairs with a pyrimidine. Ideally, DNA is replicated in exact copies by DNA polymerases during cell division in the human body or in other living organisms. DNA strands can also be replicated in vitro by means of the Polymerase Chain Reaction (PCR).

Sometimes, exact replication fails and an incorrect base pairing occurs. Further replication of the new strand produces double stranded DNA offspring containing a heritable difference in the base sequence from that of the parent. Such heritable changes in base pair sequence are called mutations.

As used herein, double stranded DNA is referred to as a duplex. When a base sequence of one strand is entirely complimentary to a base sequence of the other strand, the duplex is called a homoduplex. When a duplex contains at least one base pair which is not complimentary, the duplex is called a heteroduplex. A heteroduplex is formed during DNA replication when an error is made by a DNA polymerase enzyme and a non-complimentary base is added to a polynucleotide chain being replicated. Further replications of a heteroduplex will, ideally, produce homoduplexes which are heterozygous, i.e., these homoduplexes will have an altered sequence compared to the original parent DNA strand. When the parent DNA has a sequence which predominates in a naturally occurring population, the sequence is generally referred to as a "wild type".

Many different types of DNA mutations are known. Examples of DNA mutations include, but are not limited to, "point mutation" or "single base pair mutations" in which an incorrect base pairing occurs. The most common point mutations comprise "transitions" in which one purine or pyrimidine base is replaced for another and "transversions" wherein a purine is substituted for a pyrimidine (and visa versa). Point mutations also comprise mutations in which a base is added or deleted from a DNA chain. Such "insertions" or "deletions" are also known as "frameshift mutations". Although they occur with less frequency than point mutations, larger mutations affecting multiple base pairs can also occur and may be important. A more detailed discussion of mutations can be found in U.S. Pat. No. 5,459,039 to Modrich (1995), and U.S. Pat. No. 5,698,400 to Cotton (1997). These references and the references contained therein are hereby incorporated by reference in their entireties.

The sequence of base pairs in DNA is a code for the production of proteins. In particular, a DNA sequence in the exon portion of a DNA chain codes for a corresponding amino acid sequence in a protein. Therefore, a mutation in a DNA sequence may result in an alteration in the amino acid sequence of a protein. Such an alteration in the amino acid sequence may be completely benign or may inactivate a protein or alter its function to be life threatening or fatal. On the other hand, mutations in an intron portion of a DNA chain would not be expected to have a biological effect since an intron section does not contain code for protein production. Nevertheless, mutation detection in an intron section may be important, for example, in a forensic investigation.

Detection of mutations is therefore of great importance in diagnosing diseases, understanding the origins of disease, and the development of potential treatments. Detection of mutations and identification of similarities or differences in DNA samples is also of critical importance in increasing the world food supply by developing diseases resistant and/or higher yielding crop strains, in forensic science, in the study of evolution and populations, and in scientific research in general (Guyer, et al., *Proc. Natl. Acad. Sci. USA* 92:10841 (1995); Cotton, *TIG* 13:43 (1997)).

Alterations in a DNA sequence which are benign or have no negative consequences are sometimes called "polymorphisms". For the purposes of this application, all alterations in the DNA sequence, whether they have negative consequences or not, are defined herein as "mutations". For the sake of simplicity, the term "mutation" is used herein to mean an alteration in the base sequence of a DNA strand compared to a reference strand (generally, but not necessarily, a wild type). As used herein, the term "mutation" includes the term "polymorphism" or any other similar or equivalent term of art.

Prior to this invention, size based analysis of DNA samples was accomplished by standard gel electrophoresis (GEP). Capillary gel electrophoresis (CGE) was also been used to separate and analyze mixtures of DNA fragments having different lengths, e.g., the digests produced by restriction enzyme cleavage of DNA samples. However, these methods cannot distinguish DNA fragments which have the same base pair length but have a differing base sequence. This is a serious limitation of GEP.

Mutations in heteroduplex DNA strands under "partially denaturing" conditions can be detected by gel based analytical methods such as denaturing gradient gel electrophoresis (DGGE) and denaturing gradient gel capillary electrophoresis (DGGC). The term "partially denaturing" is defined to be the separation of a mismatched base pair (caused by temperature, pH, solvent, or other factors) in a DNA double strand while other portions of the double strand remain intact, that is, unseparated. The phenomenon of "partial denaturation" occurs because a heteroduplex will denature at the site of base pair mismatch at a lower temperature than is required to denature the remainder of the strand.

These gel-based techniques are difficult and require highly skilled laboratory scientists. In addition, each analysis requires a lengthy setup and separation. A denaturing capillary gel electrophoresis analysis can only be made of relatively small fragments. A separation of a 90 base pair fragment takes more than 30 minutes. A gradient denaturing gel runs overnight and requires about a day of set up time. Additional deficiencies of gradient gels are the difficulty of adapting these procedures to isolate separated DNA fragments (which requires specialized techniques and equipment), and establishing the conditions required for the isolation. The conditions must be experimentally developed for each fragment (Laboratory Methods for the Detection of Mutations and Polymorphisms, ed. G. R. Taylor, CRC Press, 1997). The long analysis time of the gel methodology is further exacerbated by the fact that the movement of DNA fragments in a gel is inversely proportional, in a geometric relationship, to the length of the DNA fragments. Therefore, the analysis time of longer DNA fragments can often be untenable.

In addition to the deficiencies of denaturing gel methods mentioned above, these techniques are not always reproducible or accurate since the preparation of a gel and running an analysis can be highly variable from one operator to another.

Separation of double stranded nucleic acid fragment mixtures by GEP or DGGE produces a linear array of bands, each band in the array representing a separated double stranded nucleic acid component of that mixture. Since many mixtures are typically separated and analyzed simultaneously in separate lanes on the same gel slab, a parallel series of such linear arrays of bands is produced. Bands are often curved rather than straight, their mobility and shape can change across the width of the gel, and lanes and bands can mix with each other. The sources of such inaccuracies stem from the lack of uniformity and homogeneity of the gel bed, electroendosmosis, thermal gradient and diffusion effects, as well as host of other factors. Inaccuracies of this sort are well known in the GEP art and can lead to serious distortions and inaccuracies in the display of the separation results. In addition, the band display data obtained from GEP separations is not quantitative or accurate because of the uncertainties related to the shape and integrity of the bands. True quantitation of linear band array displays produced by GEP separations cannot be achieved, even when the linear band arrays are scanned with a detector and the resulting data is integrated, because the linear band arrays are scanned only across the center of the bands. Since the detector only sees a small portion of any given band and the bands are not uniform, the results produced by the scanning method are not accurate and can even be misleading.

Methods for visualizing GEP and DGGE separations, such as staining or autoradiography are also cumbersome and time consuming. In addition, separation data is in hard copy form and cannot be electronically stored for easy retrieval and comparison, nor can it be enhanced to improve the visualization of close separations.

This MIPC process is temperature sensitive, and precise temperature control is particularly important in the MIPC separation processes described in co-pending U.S. patent application Ser. No. 09/129,105 filed Aug. 4, 1998, for example. Precise temperature control is required for maintaining both mobile and stationary phases at a partially denaturing temperature, that is, a temperature at which mismatched DNA present at the mutation site of a heteroduplex strand will denature but at which the matched DNA will remain bound into the double strand.

In many prior art HPLC applications, the HPLC separation process can be run at room temperature. However, in MIPC and in particular DMIPC, applications are run at elevated temperatures with the temperature of the column being thermostatically controlled. Prior art HPLC temperature controls were generally able to set and maintain a temperature within the range of ±1° C. and achieve equilibrium temperature within 10 minutes. The temperature control did not provide the accuracy or precision required with the MIPC process. The systems did not provide for establishing and maintaining the column and solution temperatures at the same value.

With advanced MIPC and DMIPC processes, achieving equilibrium at a new set temperature within 1 minute with a temperature control within the range of ±0.1° C. is needed. In addition, the automated oven control must provide the specific oven conditions required for each particular method or separation. Maintaining a constant temperature is especially important in quantitative analysis, since changes in temperature can seriously affect peak-size measurement. These devices usually consist of high-velocity air blowers plus electronically controlled thermostats, with configurations similar to those used in gas chromatographs. Alternatively, LC columns can be jacketed and the temperature controlled by contact heaters or by circulating fluid from a constant-temperature bath. This latter approach is practical for routine analyses, but does not meet the time response requirements, accuracy or precision of the improved high capacity systems of this invention.

SUMMARY OF THE INVENTION

It is an object of this invention to provide a column heating system in which both the temperature of the column and the solutions introduced to the column are maintained at the same precise and accurate temperatures, features required by the MIPC and DMIPC separation processes carried out therein.

It is another object of this invention to provide a column heating system in which both the temperature of the column and the solutions introduced to the column can be rapidly changed from one temperature value to another without loss of precision or accuracy as required for certain processes, e.g., empirical temperature titrations to identify an optimum denaturing MIPC temperature.

In summary, this invention is a liquid chromatography apparatus with stationary and mobile phase temperature control suitable for polynucleotide separations by MIPC and DMIPC processes. It comprises heater means having a temperature control system; a matched ion polynucleotide chromatography separation column having an inlet end; and capillary tubing having an inlet end and an outlet end. The outlet end of the capillary tubing is connected with the inlet end of the separation column, and the inlet end of the capillary tubing comprises means for receiving process liquid. The tubing has a fully extended length which is preferably from 6 to 400 cm and can be a coil. The separation column and the coil of capillary tubing are enclosed in the heater means. The temperature control system is preferably calibrated to the temperature of liquid flowing into the column.

The capillary tubing is preferably PEEK or titanium. The inlet end of the coil of capillary tubing can communicate with a prefilter, the prefilter being optionally enclosed in the heater means.

One embodiment of the liquid chromatography apparatus of this invention includes an air bath oven having a recirculating air temperature control system and a matched ion polynucleotide chromatography separation column having an inlet end and an outlet end. It includes a coil of capillary tubing having an inlet end and an outlet end, the outlet end of the capillary tubing being connected with the inlet end of the separation column, and the inlet end of the capillary tubing comprising means for receiving process liquid. The tubing preferably has a fully extended length of from 6 to 400 cm. The separation column and the coil of capillary tubing are enclosed in the air bath oven. Preferably, the inlet end of the coil of capillary tubing communicates with a prefilter, the prefilter being enclosed in air bath oven.

Preferably the apparatus air bath system includes a recirculating air temperature control system comprising a temperature sensor, a heater and a heater control. The temperature sensor is positioned in the air bath oven in the path of recirculated air and is connected to the heater control. The heater control is connected to the heater, the heater and the heater control comprising means for regulating the temperature of recirculating air in the air bath.

Also this invention includes the process of calibrating the temperature control by a direct measurement of the temperature of the liquid entering the column, such as an infrared temperature sensor measurement or use of a contact temperature sensor placed on the capillary tubing connecting the column with the means for receiving process liquid (liquid temperature sensor). A table of corresponding measures of liquid temperature and air temperature is established. First a system temperature is set by a user. Then corresponding air temperature is calculated from the table. The heater is set to this air temperature. Then the liquid temperature is read by the system control and compared to the set temperature. If the difference between the set temperature and the liquid temperature is more than allowed margin, than the heater settings must be adjusted by increasing or decreasing the heater settings by the difference between the set temperature and the liquid temperature. Then the calibration table is adjusted to register the actual set temperature and air and liquid temperatures. This procedure is repeated until the difference between the liquid temperature and the set temperature is within the allowed margin.

Further the temperature sensor can be mounted directly on the coil of capillary tubing for more accurate temperature reading.

In another embodiment of this invention, the heater means are comprised of a heat conducting block having a first primary heat transfer surface, a separation column receptacle, and a capillary coil receptacle. A separation column is positioned within the separation column receptacle in heat conducting relationship with an inner wall thereof; and a coil of capillary tubing is positioned in the capillary coil receptacle. The outer extremities of the coil are in heat conducting relationship with an inner wall of the capillary coil receptacle. The system includes a heater means, the heater means being in heat conducting relationship with said first heat transfer surface. The system preferably includes a heater control, the heater control being linked with the heat sensor and the heater means. The system can include a heat radiator, wherein the heat conducting block has a second heat transfer surface and the heat radiator is in heat conducting relationship with said second heat transfer surface.

Preferably, the heat-conducting block includes a heat sensor receptacle and a heat sensor, the heat sensor being positioned within the heat sensor receptacle in heat conducting relationship with an inner surface thereof.

The heating means can be a Peltier heating and cooling unit, the Peltier heating and cooling unit being in heat conducting relationship with said first heat transfer surface. The heater control is linked with the heat sensor and Peltier heating and cooling unit.

DETAILED DESCRIPTION OF THE INVENTION

This invention provides an HPLC system which can separate DNA fragments based on size differences by MIPC, and can also separate DNA heteroduplexes of mutant strands paired with wild type strands from homoduplexes by DMIPC to identify the presence of mutations. It can achieve these separations in an accurate, reproducible, reliable manner.

Precise temperature control of the separation column and the solutions passing therethrough is required for optimum DNA fragment separations by MIPC and mutation detection by DMIPC, application of the Matched Ion Polynucleotide Chromatography (MIPC) under the partially denaturing conditions used for separating heteroduplexes from homoduplexes in mutation detection.

Figure 1:
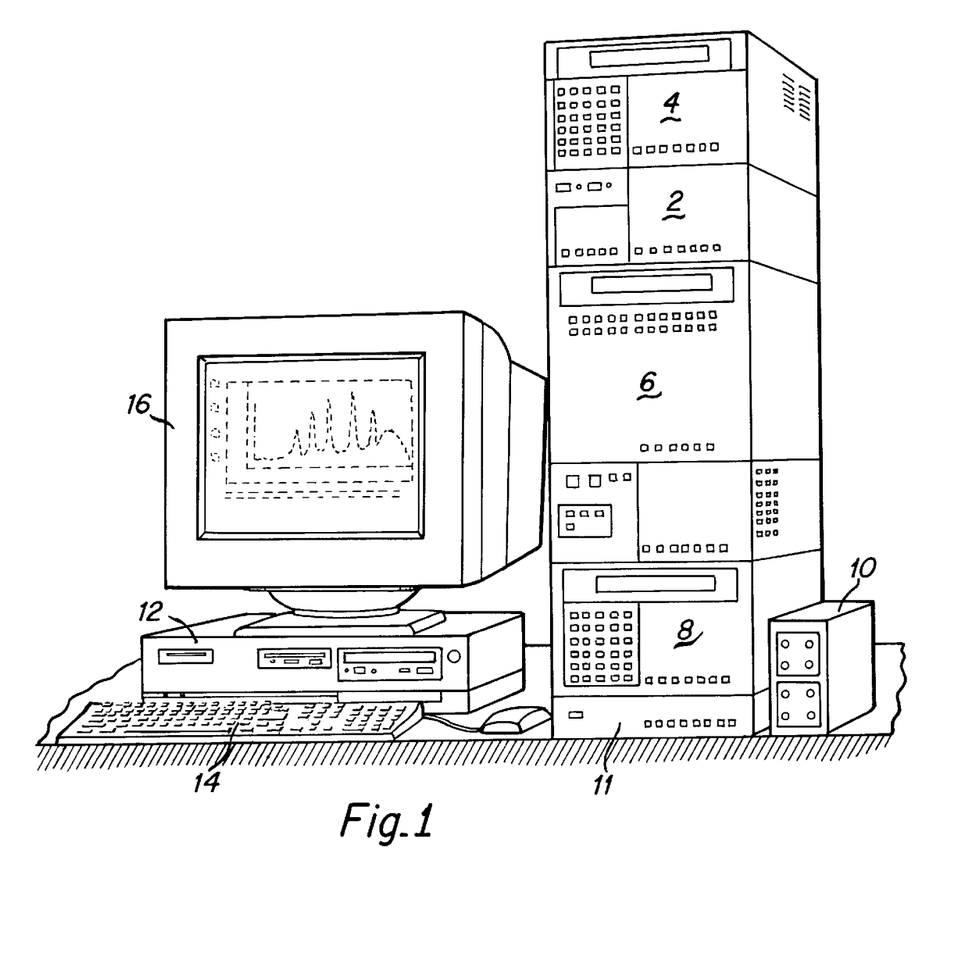
FIG. 1 is a perspective view of a HPLC DNA analyzer system suitable for use in separating DNA fragments into fractions based on size.

FIG. 1 is a perspective view of a HPLC DNA analyzer system suitable for use in separating DNA fragments into fractions based on size. The system can comprise stacked components, as shown in this presentation, or it can be integrated into a single cabinet or housing. The principal components are represented here by the column oven housing 2, which contains the separation column, and the detector housing 4 which contains a detector which measures a property of the column eluant which is a function of the concentration of the material being separated. The autosampler housing 6 contains sample vials or well trays and conventional autosampling components. The pump housing 8 contains the pumps for moving the liquid solvents, reagent solutions, and sample solutions through the column. The degasser housing 10 houses a solution degasser. The control and system monitoring features include a control interface 11, a conventional desktop computer with a CPU 12, input keyboard 14, and output monitor 16. The system can be connected to conventional printers, networks and auxiliary storage devices (not shown).

Figure 2:
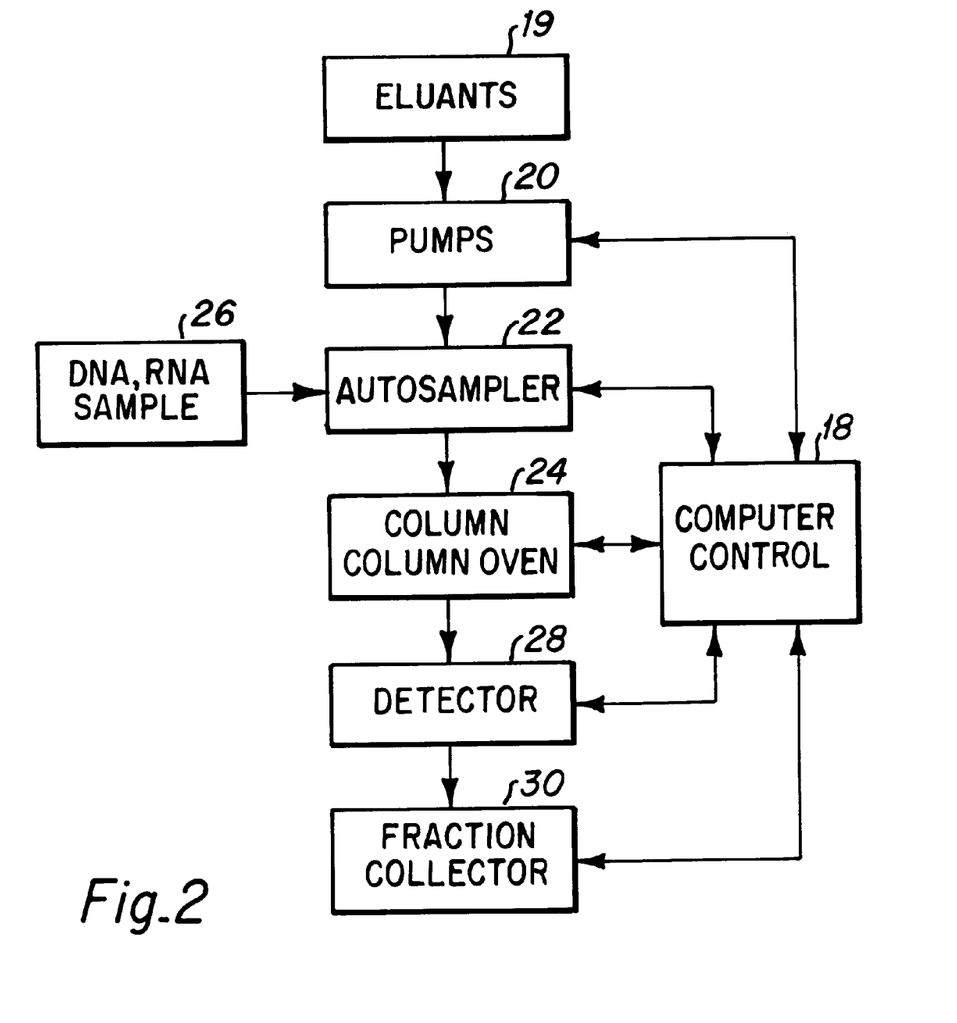
FIG. 2 is a schematic diagram of a system showing the relationship between the operating components of the DNA analyzer system.

FIG. 2 is a schematic diagram of a system showing the relationship between the operating components. Under the directions of the computer control 18, eluants 19 are moved by pumps 20 through the autosampler assembly 22 to the column and column oven 24. The eluants include liquid solvents, reagent solutions, and sample solutions which are required for the separation processes. Polynucleotide samples such as DNA fragments, RNA samples and other oligonucleotides are removed from sample containers (vials, trays or the like) in the sample source 26 and mixed with a solvent solution in the autosampler assembly 22. As shown in greater detail hereinafter, the solutions and the separation column are brought to a desired controlled temperature in the column oven 24.

The separation column separates polynucleotide components passing therethrough into size-based fractions, and these fractions are carried in the eluant solutions passing through the detector 28 and to the fraction collector 30.

The system components, with the exception of the oven, are conventional HPLC system components which are readily available from domestic and foreign sources. The specialized columns are combined with these components in the commercial WAVE DNA Fragment Analyzer system available from Transgenomic, Inc. (Omaha, Nebr.).

Details about the MIPC and DMIPC processes, the apparatus and separation columns are fully described in U.S. Pat. Nos. 5,585,236, 5,772,889, 5,795,976 and co-pending U.S. patent applications Ser. Nos. 09/058,580, 09/058,337, 09/129,105, the entire contents of all of which are hereby incorporated by reference.

Figure 3:
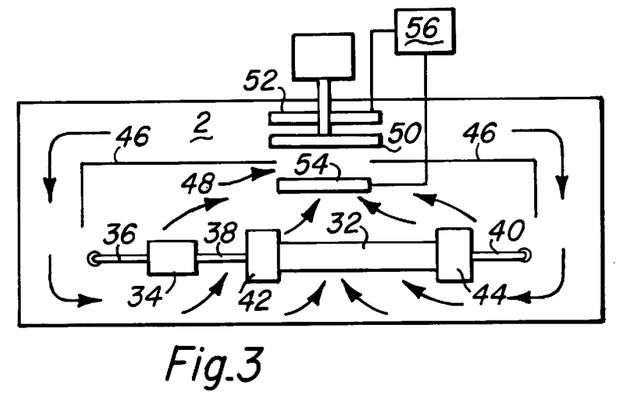
FIG. 3 is a view of a conventional prior art HPLC DNA analyzer column oven.

FIG. 3 is a view of a conventional prior art HPLC DNA analyzer column oven. Housing 2 contains separation column 32, prefilter 34, and capillary tube sections 36, 38 and 40. The separation column 32 has an inlet end 42 and an outlet end 44. The inlet end 42 is connected to the prefilter 34 by capillary tube 38. The prefilter 34 communicates with the autosampler through capillary tube 36. The outlet conduit 40 leads from the outlet end 44 of the column 32 to the analyzer unit. In traditional HPLC systems, the dead volume represented by the capillary tubing 36, 38, and 40 and the prefilter 34 reduced the separation efficiency, causing peak broadening. Therefore, the lengths of the capillaries were traditionally minimized.

Air circulating through the housing 2 and passing over the prefilter 34, column 32, and capillary segments 36, 38 and 40 must establish and maintain these components and the liquid passing through at a selected temperature. The housing 2 is separated into a process section and a heater fan section by wall 46. Air exits from the process section through an exhaust port 48 in the wall 46, drawn by fan 50, passes through heater elements 52 and returns to the process section. The exit air temperature is monitored by temperature sensor 54, the sensor 54 having a lead connecting with a conventional heater temperature controller 56.

If sufficient time passes to equilibrate the temperature of the system and system components, the temperature of the tubing, prefilter and column components can be maintained within the range of ±1° C. by the circulating air. However, air and the system components have a severely limited opportunity to heat the liquid passing into the column. Temperature uniformity is compromised during operation of the system by the heat transfer to or from the solutions passing through the capillary tubing and the column.

Figure 4:
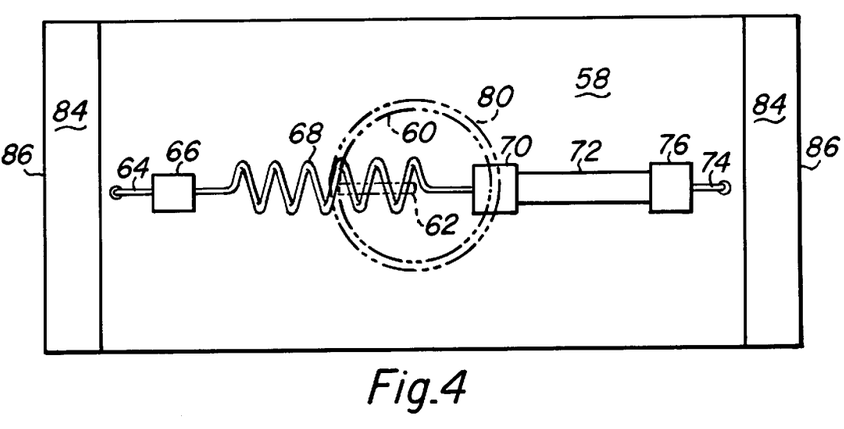
FIG. 4 is a front view of the separation compartment of an improved HPLC DNA analyzer column oven according to this invention.

We have found that the MIPC system is relatively insensitive to the dead-space in the capillary tubing leading from the sample injector and the separation column. In fact, dead volume up to several milliliters between the sample injector and the separation column are acceptable in MIPC systems. The only limitation in dead volume space is its effect on the total time necessary to forms mobile phase gradient. Unlike HPLC, duality of the separation is not affected by dead space. As a consequence, the capillary tubing can be lengthened without compromising the separation by the column. This feature has permitted the oven modifications shown in FIGS. 4 and 5. FIG. 4 is a front view of the process compartment of a HPLC DNA analyzer column oven according to this invention, and FIG. 5 is a top view of the HPLC DNA analyzer column oven shown in FIG. 4.

Figure 5:
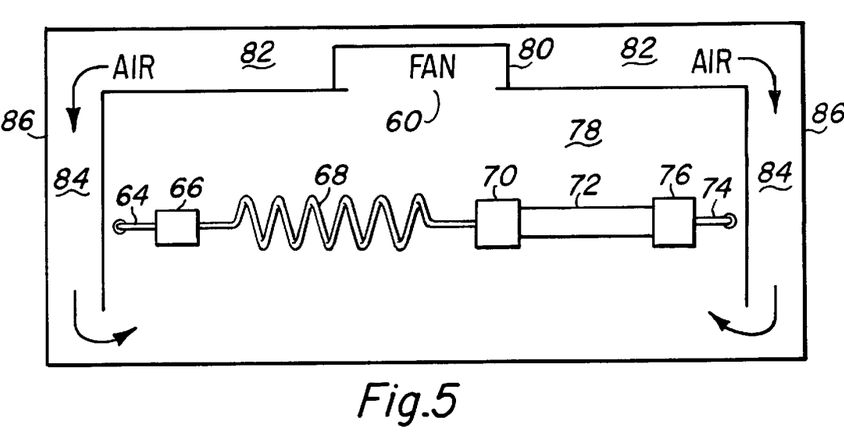
FIG. 5 is a top view of the HPLC DNA analyzer column oven shown in FIG. 4.

The process compartment in the embodiment shown in FIGS. 4 and 5 is divided from the heating compartment by wall 58 in which air exhaust port 60 is positioned. A temperature sensor such as thermister 62 is positioned in the port 60 to monitor the temperature of the air passing through the port.

Capillary tubing 64 leads from the sample injector (not shown) to a prefilter 66. Prefilter 66 is an inline filter or guard cartridge such as described in U.S. Pat. No. 5,772,889. It removes contaminants from the incoming liquid. An elongated coil 68 of capillary tubing has an inlet end communication with prefilter 66 for receiving process liquid therefrom. The elongated coil 68 has an outlet end communicating with the inlet end 70 of a separation column 72. Separation column 72 contains MIPC separation media described in U.S. Pat. No. 5,585,236 and co-pending U.S. patent applications Ser. Nos. 09/058,580, 09/058,337, 09/183,123, 09/183,450. Outlet tubing 74 leads from the outlet end 76 of the separation column 72 to a detector (not shown).

The coil 68 is a liquid heating coil made of a DNA compatible, multivalent cation free tubing which has the desired heat conductivity. Titanium or PEEK described in U.S. Pat. No. 5,772,889 and application Ser. No. 09/081,040 are preferred because they can be freed of multivalent ion contamination. The length and diameter of tubing used is any length which is sufficient to enable liquid passing therethrough to reach the equilibrium temperature of air in the processing compartment. A length of from 6 to 400 cm and a tubing ID of from 0.15 to 0.4 mm is usually sufficient. Since the length of tubing 68 does not degrade the separation of components achieved by the system, the length can be selected based on the length required to achieve effective heating of the process liquids.

Referring to FIG. 5, the air is heated and recycled in the same manner as described in FIG. 3. Air from the processing compartment 78 passes through the opening 60 in wall 58, through a heater/fan system 80 for temperature adjustment. The adjusted air received by the heating compartment 82 recycles back to the processing compartment 78 along the passageways 84 defined by the spacing between the wall 58 and the outer oven wall 86.

The heating coil in the embodiment shown in FIGS. 4 and 5 provides a temperature accuracy to within the range of ±0.2° C. and reduces the temperature equilibrium time between temperature settings to below 5 minutes for temperature changes of 5° C. and below 2 minutes for temperature changes for up to 1° C.

Figure 6:
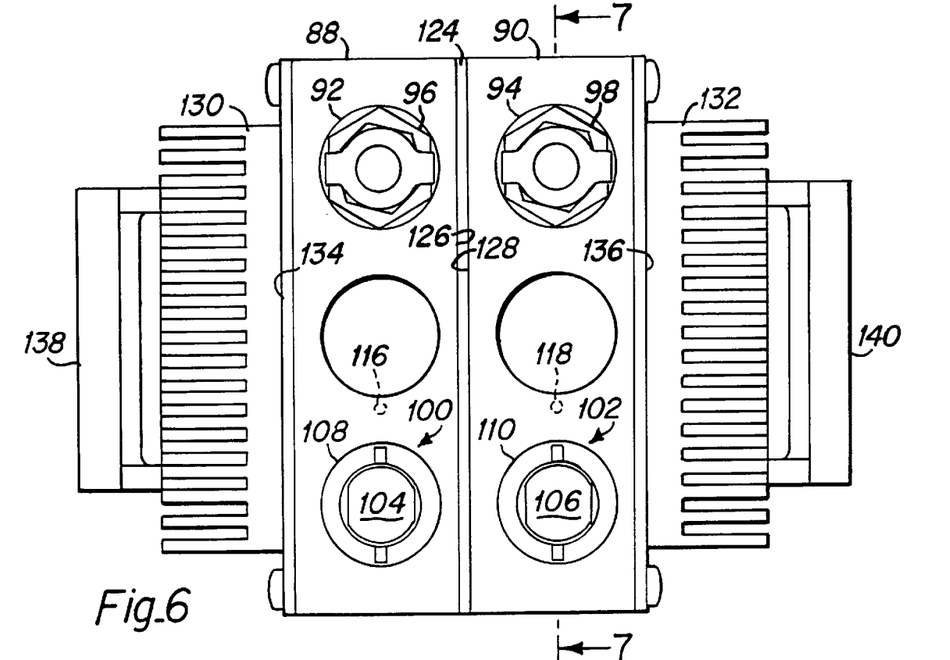
FIG. 6 is an end view of the compact dual column heater embodiment of this invention.
Figure 7:
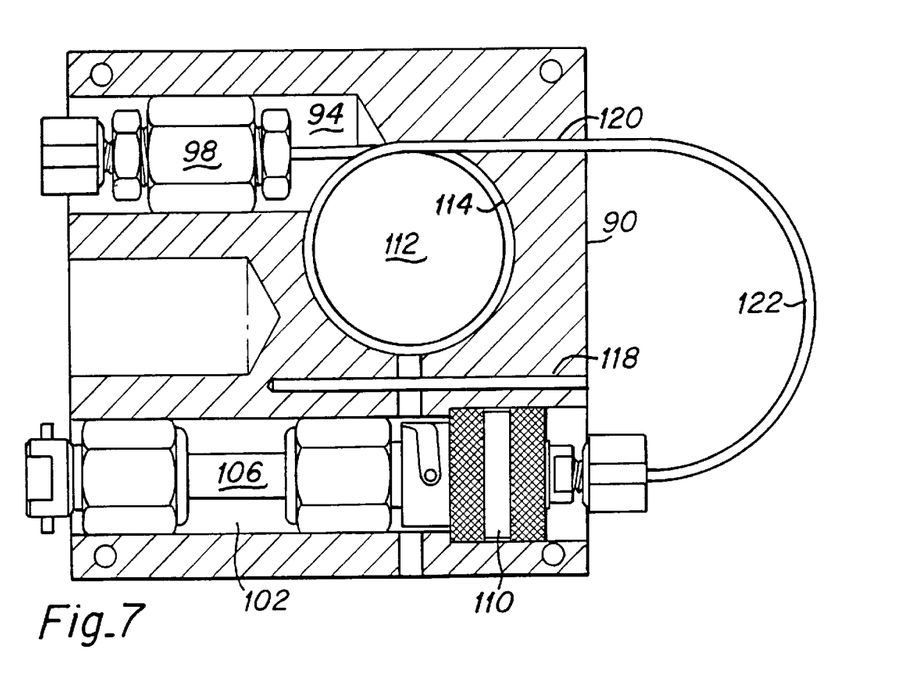
FIG. 7 is a cross-sectional view taken along the line 7—7 in FIG. 6.

FIG. 6 is an end view of a preferred compact dual column heater embodiment of this invention, and FIG. 7 is a cross-sectional view taken along the line 7—7 in FIG. 6. This embodiment uses direct metal-to-metal conduction of heat to and from the system components and does not rely on an air bath to achieve temperature changes and accuracy.

This preferred embodiment is shown for a two column system, although it could be used for a single column, if desired. It comprises heat conducting blocks (88,90) having receptacles sized and shaped to receive the system components. Filter cavity or prefilter receptacles (92,94) have inner surfaces which are sized to receive prefilters (96,98) and establish heat transfer contact with the outer surfaces thereof. Separation column receptacles (100,102) have inner surfaces sized to receive respective separation columns (104,106) and separation column couplers (108,110) which connect capillary tubing to the respective separation columns. Receptacles (100,102) are sized and shaped to establish heat transfer contacts between the inner heat transfer surfaces of blocks (88,90) and the separation column components received therein. Capillary coil receptacles 112 (one is shown in FIG. 7) have an inner surface which is shaped to receive a coil of capillary tubing 114 (one is shown in FIG. 7) and to establish heat transfer contact with the outer surface thereof. In the embodiment shown in these figures, receptacles (92, 94) and (100, 102) are cylindrical holes with approximately parallel central axes lying in a common plane. It would be readily apparent to a person skilled in the art that other configurations are equally suitable and all configurations are considered to be within the scope of this invention.

Temperature sensor receptacles (116, 118) are provided in heat conducting blocks (88, 90). Capillary receptacle passageways 112 for receiving connecting tubing 122 in a heat-conducting relationship are also provided in the heating-conducting block (88, 90). The capillary coil receptacles 112 are shown in this figure to be cylindrical cavities with their axes perpendicular to the axes of receptacles (92, 94) and (100, 102). Optionally, a conductive metal cylinder (not shown) can be positioned within the capillary coils in heat conducting contact with the inner surfaces thereof to increase heat transfer area between the metal block heating assembly and the liquid in the coils.

A KAPTON resistance heater or other type of heating unit 124 is positioned between and in heat-conducting contact with surfaces 126 and 128 of heating blocks (88, 90) to transfer heat to the heat-conducting blocks. Heat sinks (130, 132) are positioned in heat-conducting relationship with opposed cooling surfaces (134, 136) of the heat conduct blocks (88, 90) to remove heat therefrom. Cooling fans 138 and 140 in a heat removal relationship with the heat sinks 130 and 132 and are activated to accelerate heat removal therefrom.

The heat conducting blocks 88 and 90, and the heat sinks 130 and 132 are made of a material having high heat conductivity such as aluminum or copper, although they can be made of other heat-conducting solids such as ferrous metals or any other solid material having the requisite heat conductivity. Heat pipes can also be used as heat sinks.

The capillary tubing can be made of DNA compatible PEEK or titanium, although titanium is preferred for maximum heat transfer efficiency. With this improved heat transfer, the capillary coil can have a fully extended length as short as 5 cm although a minimum coil length of 10 cm is preferred. A longer coil of PEEK would be required to achieve the same heat transfer as titanium capillary tubing.

The system shown in FIG. 6 and 7 comprises two systems in mirror image. It will be readily apparent that for a single column, half the system would be sufficient and is intended to be included within the scope of this invention.

The position, alignment and spacing of the receptacles are not a critical feature of this invention. Any alignment and configuration which provides a compact and heat-transfer efficient result is intended to be included within the scope of this invention. Heat transfer isolation of the heating and cooling unit from the casing is preferred.

The embodiments of the invention shown in FIGS. 6 and 7 provide a compact heater which is more responsive to heater controls, provides rapid changes from one temperature platform to another, and maintains a temperature accuracy within ±0.5° C. of a set temperature. The heat transfer rate obtained with the metal-to-metal contact between the heating block and the elements being heated is far greater than can be obtained in an air bath system, providing the more rapid response to a changed temperature and greater temperature accuracy. It also allows process liquid temperature adjustment with a shorter capillary tubing coil.

Figure 8:
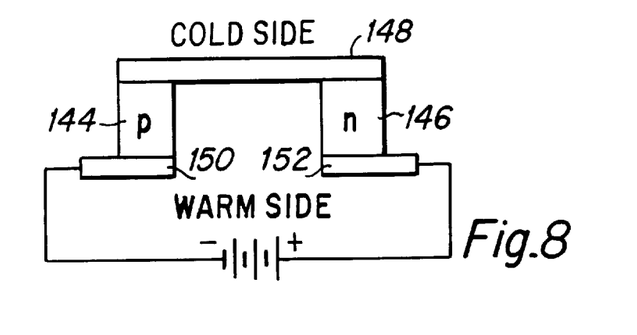
FIG. 8 is a schematic view of a Peltier heater.

FIG. 8 is a schematic view of a Peltier heater. With the use of semiconductor materials in Peltier elements, relatively high temperature differences can be achieved. Each Peltier element is made of a p- or n-type semiconductor material which is linked to a copper bridge. In this view, element 144 is a conventional p-type doped semiconductor material such as silicon and element 146 is a conventional n-type doped semiconductor material. Elements 148, 150 and 152 are copper bridges. With the negative voltage on the p-doped side and the positive voltage on the n-doped side, copper bridge 148 is cooled and copper bridges 150 and 152 are heated. If the voltage is reversed, the copper bridge 148 is heated and the copper bridges 150 and 152 are cooled. Thus with simple voltage changes, the copper bridge 148 can be a source of both heating and cooling to rapidly and precisely regulate the temperature of a metal block in a heat conductive relationship therewith.

Figure 9:
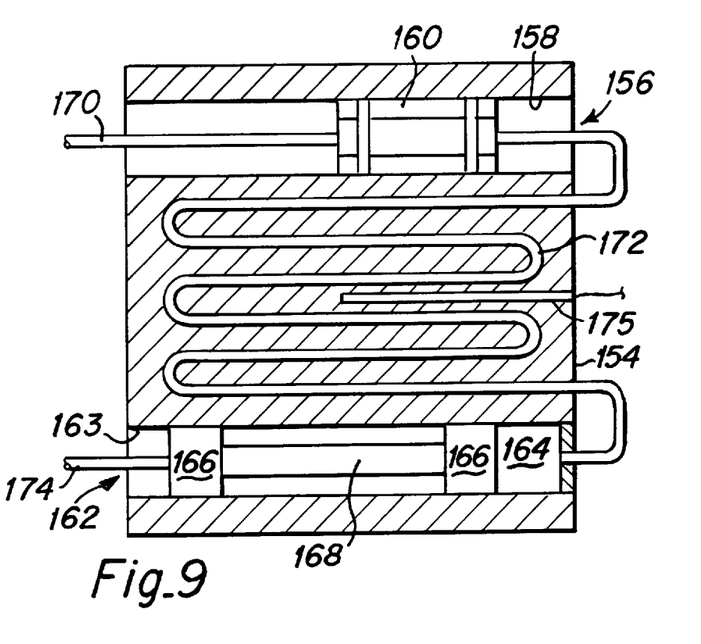
FIG. 9 is a schematic view of a preferred Peltier heater/cooler embodiment of this invention.

FIG. 9 is a schematic view of a preferred Peltier heater/cooler embodiment of this invention. Heating block 154 is in conductive contact with a Peltier heating element (not shown) for heating or cooling required to reach and maintain a desired temperature. Channel 156 is a prefilter receptor having an inner surface 158 in heat conductive relationship with prefilter 160. Channel 162 is a column and column guard receptor having an inner surface 163 in heat conductive relationship with coupler 164 and end nut elements 166 of separation column 168. Capillary tubing 170 communicates with the prefilter 160 and the sample and solution sources (not shown). Capillary tubing 174 from the outlet of the separation column 168 communicates with an analyzer (not shown). Capillary tubing 172 connects the outlet end of the prefilter 160 with the coupler 164, which in turn communicates with the separation column 168. Capillary tubing 172 is received in a labyrinth-like configuration of channels in the heating block 164 to provide increased capillary length and surface contact between the capillary tubing 172 and the heating block 154. The configuration of the labyrinth can be any configuration which provides an adequate capillary length and surface contact, including circular loops and capillary placement of more than one pass per channel.

The capillary tubing 172 can be PEEK or titanium, titanium being preferred because of its high heat conductivity. The heating block 154 can be any heat conductive metal. Aluminum or copper are preferred because of their higher heat conductivity, although ferrous metals such as steel can be used.

Temperature sensor 175 is positioned in the center of the block in a corresponding receptor channel.

The Peltier heater is controlled with a conventional temperature and control system (not shown) such as the systems used in Peltier thermocyclers. The temperature accuracy achieved by this Peltier-heated block is ±0.5° C.

Figure 10:
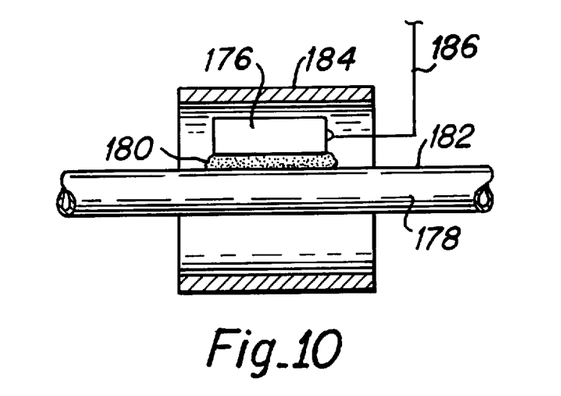
FIG. 10 is a schematic view of a temperature sensor component for calibration of the temperature controls or for use as the temperature sensor in the oven shown in FIG. 4.

FIG. 10 is a schematic view of a process liquid temperature sensor.

Temperature sensor 176 is mounted on capillary tubing 178 with a layer of thermally conductive grease 180 between the sensor 176 and an outer surface 182 of the tubing 178. The capillary tubing is preferably titanium. The sensor 30 176 is further enclosed in an insulation sleeve 184. A electrical lead 186 connects the sensor 176 to the temperature controls (not shown). Positioning the temperature sensor 176 directly on the outer surface of the capillary tubing 178 increases the accuracy of temperature measurement of the liquid flowing through the tubing A layer of thermally-conductive grease between the sensor 178 and the tubing 178 increases the area of thermal contact between the sensor and the tubing and further improves the accuracy of temperature reading.

The temperature sensor of FIG. 10 can also be used for calibrating a temperature sensor mounted in the air bath oven by comparing the data from the process liquid temperature sensor to the data from the temperature sensor located in the air bath oven and calculating the deviation of the two.

The temperature sensors 62 shown in FIG. 4, the sensors positioned in the receptors 116 and 118 shown in FIG. 6 and the temperature sensor 175 shown in FIG. 9 are optimally calibrated to the temperature of the liquid passing through the capillary tubing and separation column.

This invention is further described in the following specific but non-limiting examples. In these examples, procedures described in the past tense in the examples below have been carried out in the laboratory. Procedures described in the present tense have not been carried out in the laboratory and are constructively reduced to practice with the filing of this application.

EXAMPLE 1

A WAVE brand DNA fragment separation system from Transgenomic Inc. was combined with an oven unit produced from a Model PTC200 M J Research thermocycler. The thermocycler was modified to contain a DNASep™ column and preheat lines (1 50 cm×0.33 mm ID) made of PEEK tubing. The preheat tubing was interwound between the PCR tube wells (i.e., physically placed around the wells themselves and in thermal contact with the 96-well heating block) and then was connected to the column placed in a cavity machined out of the thermocycler. The oven response was high with approximately 10 seconds required to reach a set temperature. It took about 2 minutes for the fluid to reach the set temperature. This response was much faster than the air bath oven of FIGS. 4 and 5. The oven was cooled and heated with a Peltier unit, so that increases and decreases in temperature were effected rapidly.

While the foregoing has presented specific embodiments of the present invention, it is to be understood that these embodiments have been presented by way of example only. It is expected that others will perceive and practice variations which, though differing from the foregoing, do not depart from the spirit and scope of the invention as described and claimed herein.

What invention claimed is:

1. A liquid chromatography apparatus for polynucleotide separations by MIPC and DMIPC processes comprising:

heater means having a temperature control system;

a matched ion polynucleotide chromatography separation column having an inlet end;

a length of capillary liquid heating tubing having an inlet end and an outlet end, the outlet end of the capillary tubing being connected with the inlet end of the separation column, and the inlet end of the capillary tubing comprising means for receiving process liquid, the tubing having a fully extended length of from 6 to 400 cm the length and diameter of tubing being sufficient to enable liquid passing therethrough to reach an equilibrium temperature;

the separation column and the coil of capillary tubing being positioned in the heater means; and the temperature control system being calibrated to the temperature of liquid flowing into the separation column.

2. A liquid chromatography apparatus of claim 1 wherein the capillary tubing is PEEK or titanium.

3. A liquid chromatography apparatus of claim 1 wherein the inlet end of the coil of capillary tubing communicates with a prefilter, the prefilter being enclosed in the heater means.

4. A liquid chromatography apparatus for polynucleotide separations by MIPC and DMIPC processes comprising:

an air bath oven having a recirculating air temperature control system;

a matched ion polynucleotide chromatography separation column having an inlet end;

a length of capillary liquid heating tubing having an inlet end and an outlet end, the outlet end of the capillary tubing being connected with the inlet end of the separation column, and the inlet end of the capillary tubing comprising means for receiving process liquid, the tubing having a fully extended length of from 6 to 400 cm the length and diameter of tubing being sufficient to enable liquid passing therethrough to reach an equilibrium temperature; and the separation column and the coil of capillary tubing being enclosed in the air bath oven and exposed to air therein.

5. A liquid chromatography apparatus of claim 4 wherein the capillary tubing is PEEK or titanium.

6. A liquid chromatography apparatus of claim 4 wherein the inlet end of the coil of capillary tubing communicates with a prefilter, the prefilter being enclosed in air bath oven.

7. A liquid chromatography apparatus of claim 4 wherein the recirculating air temperature control system comprises a temperature sensor, a heater and a heater control, the temperature sensor being positioned in the air bath oven in the path of recirculated air and being connected to the heater control, the heater control being connected to the heater, the heater and the heater control comprising means for regulating the temperature of recirculating air in the air bath.

8. A liquid chromatography apparatus of claim 4 wherein the recirculating air temperature control system comprises a temperature sensor, a heater and a heater control, the temperature sensor being positioned in direct contact with the capillary tubing and being connected to the heater control, the heater control being connected to the heater, the heater and the heater control comprising means for regulating the temperature of recirculating air in the air bath.

* * * * *